United States Patent [19]

Raspanti

[11] Patent Number: 5,250,292
[45] Date of Patent: Oct. 5, 1993

[54] USE OF CYCLIC ORGANIC AMINES IN DERMATOLOGICAL COMPOSITIONS

[75] Inventor: Giuseppe Raspanti, Bergamo, Italy

[73] Assignee: Sigma Prodotti Chimici S.p.A., Milan, Italy

[21] Appl. No.: 897,403

[22] Filed: Jun. 12, 1992

[30] Foreign Application Priority Data

Jul. 5, 1991 [IT] Italy ......................... MI91 A 001866

[51] Int. Cl.⁵ ..................... A61K 31/74; A61K 31/445
[52] U.S. Cl. ................................ 424/78.03; 424/78.02; 424/401; 514/847; 514/315
[58] Field of Search .................. 424/401, 78.02, 78.03; 514/315, 847

[56] References Cited

U.S. PATENT DOCUMENTS

| 4,322,531 | 3/1982 | Karrer | 546/22 |
| 4,552,885 | 11/1985 | Gabriele | 514/315 |
| 4,609,698 | 9/1986 | Karrer | 546/187 |
| 4,960,774 | 10/1990 | Rentzea | 514/315 |

*Primary Examiner*—Thurman K. Page
*Assistant Examiner*—Sally Gardner
*Attorney, Agent, or Firm*—Griffin Butler Whisenhunt & Kurtossy

[57] ABSTRACT

The use of cyclic organic amines, as free radicals deactivators, in the preparation of cosmetic and dermatological compositions.

4 Claims, No Drawings

USE OF CYCLIC ORGANIC AMINES IN DERMATOLOGICAL COMPOSITIONS

The present invention relates to the use, as agents useful in cosmetics and dermatology, of the compounds of formula I

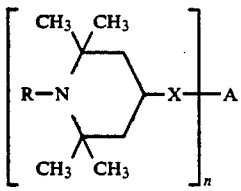

wherein

R is selected from hydrogen, $C_1$-$C_{12}$ alkyl, benzyl, $C_2$-$C_4$ hydroxyalkyl, the group of formula II $$-(CH_2\text{-}CH_2\text{-}O)_m-H \qquad (II)$$

wherein m is an integer from 2 to 20;

X is selected from oxygen, $-NR_1-$ in which $R_1$ is hydrogen, $C_1$-$C_{12}$ alkyl, the group of formula II, $C_5$-$C_6$ cycloalkyl;

n is an integer from 1 to 4;

A is an alkyl residue with a valence from 1 to 4, a mono- or polyacyl group deriving from carbonic acid or from an organic mono or polycarboxylic acid, a carbamoyl or dicarbamoyl group deriving from a mono or diisocyanate, a group of formula III or IV

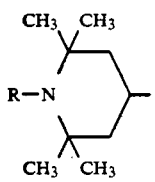

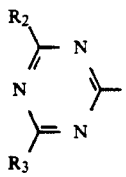

wherein R is as defined above, $R_2$ and $R_3$ can be the same or different and they are a group of formula V

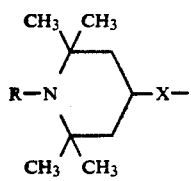

the group $-OR_1$; $-NRR_1$, wherein X, R and $R_1$ are as defined above.

Examples of an alkyl residue with valence from 1 to 4 are:
  valence 1 = straight or branched $C_1$-$C_{18}$ alkyl;
  valence 2 = straight or branched $C_2$-$C_{12}$ alkylene; such as

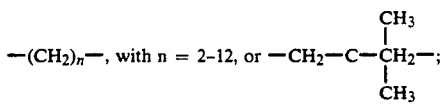

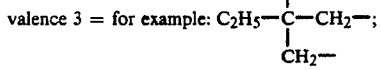

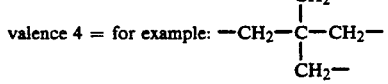

It is now believed that the cause of most of the alterations which lead to ageing of the skin are to be attributed to the action of endogenic and exogenic free radicals. On this point, dermatology has in recent years increasingly concerned itself with the processes and causes which lead to the formation of these highly reactive chemical groups, with their toxic effects and with possible defence mechanisms.

Apart from some chemical agents such as pharmaceuticals, physical factors, such as heat, light, UV radiation, supersonic waves and ionising radiation lead to the formation of free radicals.

Owing to their high reactivity, free radicals are capable of reacting easily with other neighbouring molecules, to generate further free radicals; a chain reaction thus takes place and continues to generate radicals until it is interrupted by combination with a chemical group which effects the formation of a stable molecule.

This mechanism explains the destructive action of free radicals: in fact, they can bind to the elements of the cell, such as the nucleus, the proteins and particularly the membrane; consequently, alterations which disturb the normal metabolism appear in the cells.

The adverse action of free radicals on the skin tissue consists in an attack on the cell membranes, which causes a degradation of the fibres in the connective tissue, such as collagen and elastin, which are responsible for the "tautness" and softness of young skin; the consequence is ageing of the skin, which manifests itself in the appearance of dryness, scaling and wrinkles.

In nature, there are scavengers or deactivators of free radicals; these are enzymes present in skin tissue, such as superoxide dismutase or catalase.

These are not always sufficient for total blocking of the free radicals present, which can then exert their devastating action on the skin tissue, which thus ages, losing its smooth and soft appearance.

A few substances have been proposed as free radical deactivators against skin ageing, such as, for example, vitamin E, 6-hydroxy-2,5,7,8-tetramethylchroman-2-carboxylic acid, 13-cis-retinoic acid and 6-ethoxy-1,2-dihydro-2,2,4-trimethylquinoline. However, these have not proved to be very effective.

Among the compounds of formula I, preferably used are the following:
4-acetoxy-2,2,6,6-tetramethylpiperidine
4-lauryloxy-2,2,6,6-tetramethylpiperidine
4-stearyloxy-2,2,6,6-tetramethylpiperidine
4-benzoyloxy-1,2,2,6,6-pentamethylpiperidine
4-p-chlorobenzoyloxy-2,2,6,6-tetramethylpiperidine
4-(or-toluyloxy)-1-(2-hydroxyethyl)-2,2,6,6-tetramethylpiperidine 4-isonicotinyloxy-2,2,6,6-tetramethylpiperidine
4-methoxy-2,2,6,6-tetramethylpiperidine
4-dodecyloxy-2,2,6,6-tetramethylpiperidine
4-benzyloxy-2,2,6,6-tetramethylpiperidine
4-propylcarbamoyloxy-2,2,6,6-tetramethylpiperidine
4-phenylcarbamoyloxy-1,2,2,6,6-pentamethylpiperidine
4-acetamido-1-(2-hydroxypropyl)-2,2,6,6-tetramethylpiperidine
4-stearamido-2,2,6,6-tetramethylpiperidine
4-(p-tert-butylbenzamido)-1,2,2,6,6-pentamethylpiperidine
4-acrylamido-2,2,6,6-tetramethylpiperidine
4-cyclohexylamino-2,2,6,6-tetramethylpiperidine
4-octylamino-1,2,2,6,6-pentamethylpiperidine
1-propyl-3-(2,2,6,6-tetramethyl-4-piperidinyl)urea
1-phenyl-3-(1-benzyl-2,2,6,6-tetramethyl-4-piperidinyl)urea
N,N-bis-(1,2,2,6,6-pentamethyl-4-piperidinyl)methylamine
bis-(2,2,6,6-tetramethyl-4-piperidinyl)carbonate
bis-(2,2,6,6-tetramethyl-4-piperidinyl)sebacate
bis-(1,2,2,6,6-pentamethyl-4-piperidinyl)oxalate
bis-(2,2,6,6-tetramethyl-4-piperidinyl)adipate
bis-(1-hydroxyethyl-2,2,6,6-tetramethyl-4-piperidinyl)-terephthalate
1,2-bis-(2,2,6,6-tetramethyl-4-piperidinyloxy)ethane
bis-(2,2,6,6-tetramethyl-4-piperidinyl)-hexamethylene-1,6-dicarbamate
N,N'-bis-(2,2,6,6-tetramethyl-4-piperidinyl)sebacamide
1,3-bis-(1,2,2,6,6-pentamethyl-4-piperidinyl)urea
2-butylamino-4,6-bis-[(2',2',6',6'-tetramethylpiperidinyl-4')-butylamino]-1,3,5-triazine
2-tert-octylamino-4,6-bis-[2',2',6',6'-tetramethyl-piperidinyl-4'-amino]-1,3,5-triazine 2-methoxy-4,6-bis-[1',2',2',6',6'-pentamethylpiperidinyl-4'-oxy]-1,3,5-triazine
2,4-bis-[2',2',4',4-tetramethylpiperidinyl-4-oxy]-6-[(2'',2'',6'',6''-tetramethylpiperidinyl-4'')-butylamino]-1,3,5-triazine
tris-(2,2,6,6-tetramethyl-4-piperidinyl)-benzene-1,3,5-tricarboxylate N,N',N''-tris-(1,2,2,6,6-pentamethyl-4-piperidinyl)-benzene- 1,3,5-tricarbonamide
2,4,6-tris-[(2',2',6',6'-tetramethylpiperidinyl-4')butylamino)]-1,3,5-triazine
2,4,6-tris-(1',2',2',6',6'-pentamethylpiperidinyl-4'-oxy)-1,3,5-triazine
tetra-(2,2,6,6-tetramethyl-4'-piperidinyl)-benzene-1,2,4,5-tetracarboxylate
tetra-(2',2',6',6'-tetramethyl-4-piperidinyl)-butane-1,2,3,4-tetracarboxylate.

The dermatological compositions for the treatment of the skin can be in form of lotions, ointments, creams, emulsions, gels, oils, which are used as moisturizing, tonifying, detergent agents both for day and night uses.

Preferably, these preparations are emulsions of the oil-in-water kind, and they can contain preservatives, emulsifiers, thickening agents, antioxidants, emollients, solvents, UV absorbents, perfumes, dyes or other substances generally used in dermatological compositions.

Generally the compositions, according to the present invention, can contain from 0.05 up to 10% and preferably from 0.1 to 5% of the free radical deactivators of formula I.

Of course the compounds of formula I can be contained in the compositions of the invention also together with other radical deactivators, such as vitamin E, or other active principles useful for the treatment of the skin.

The following examples illustrate the invention.

EXAMPLE 1

Moisturizing Cream

A solution of 0.3 g of 4-benzoyloxy-2,2,6,6-tetramethylpiperidine in 6 g of polyethylene glycol 400 is prepared heating to 60° C; the resulting solution is added with 0.15 g of methyl paraben (methyl p-hydroxybenzoate) and 0.05 g of propyl paraben. Separately, a mixture of 15 g of vaseline and 8 g of glyceryl monostearate is prepared and added to the above obtained solution, at 80° C. After that, the oily phase is added with 70.5 g of water pre-heated at 80° C., under strong stirring, so as to obtain an emulsion, keeping stirring until temperature is decreased to 30° C.

EXAMPLE 2

Lipophilic Gel 6 g of high-melting paraffin and 3.6 g of sorbitan tristearate (Span 65$^R$) are melted together and heated to 100° C., the melted mixture is added, under slow stirring, to 80.3 g of vaseline oil pre-heated to 100° C., then it is quickly cooled to 50° C. to obtain a gel. This gel is added with a solution of 0.1 g of 4-stearamido-2,2,6,6-tetramethylpiperidine in 10 g of polyethylene glycol 400 previously prepared, mixing until homogeneity.

EXAMPLE 3

Sun Cream

A mixture of 10 g of cyclodimeticon/dimeticon copolymer (Dow Corning Q2-3225 C), 10 g of cyclometicon (Dow Corning 344), 0.5 g of polysorbate 20 (Tween 20$^R$), 3 g of 2-hydroxy-4-methoxybenzophenone, 5 g of 2-ethylhexyl p-dimethylaminobenzoate and 0.2 g of 2,4,6 -tris-(2',2',6',6'-tetramethylpiperidinyl-4'-butylamino)-1,3,5-triazine is prepared. This mixture is added to a solution prepared previously, consisting of 0.2 g of 1,1'-methylene-bis-3-(3-hydroxymethyl-2,4-dioxy-imidazolidinyl)urea, 0.05 g of methyl paraben and 71.05 g of water.

EXAMPLE 4

Face Make-up

A mixture is prepared, heating to 75° C. 78.4 g of water, 4.5 g of glycerin, 0.6 g of 2-pyrrolidone-5-carboxylic acid and 0.2 g of methyl paraben. This mixture is added to a second mixture, previously prepared, consisting of 3 g of octyl palmitate, 1 g of dimeticon, 4.5 g of polysorbate 60 (Tween 60$^R$), 0.1 g of propyl paraben, 7.5 g of glyceryl monostearate and 0.2 g of bis-(1,2,2,6,6-pentamethyl-4-piperidinyl)-adipate.

EXAMPLE 5

Ointment

A mixture of 0.1 g of 1,3-bis-(1,2,2,6,6-pentamethyl-4-piperidinyl)urea, 5 g of $C_{12}$-$C_{15}$ alcohols benzoate and 0.5 g of titanium dioxide is prepared. The resulting dispersion is subsequently added to 4.4 g of vaseline oil gelled with polyethylene glycol 6000, stirring to homogeneity.

I claim:

1. Cosmetic and dermatological compositions useful as an anti-aging treatment of the skin consisting of at least one compound of the formula I

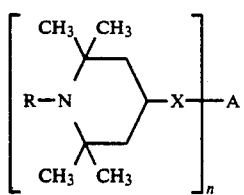 (I)

wherein:
R is selected from hydrogen, $C_1$-$C_{12}$ alkyl, benzyl, $C_2$-$C_4$ hydroxyalkyl, the group of formula II $$-(CH_2-CH_2-O)_m-H \quad (II)$$

wherein m is an integer from 2 to 20;
X is selected from oxygen, $-NR_1-$ in which $R_1$ is hydrogen, $C_1$-$C_{12}$ alkyl, the group of formula II, $C_5$-$C_6$ cycloalkyl;
n is an integer from 1 to 4;
A is an alkyl residue with a valence from 1 to 4, a mono- or polyacyl group deriving from carbonic acid or from an organic mono- or polycarboxylic acid, a carbamoyl or dicarbamoyl group deriving from a mono- or diisocyanate, a group of formula III or IV

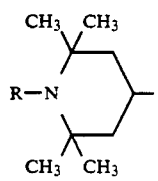 (III)

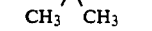

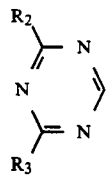 (IV)

wherein R is as defined above, $R_2$ and $R_3$ can be the same or different and are a group of formula V

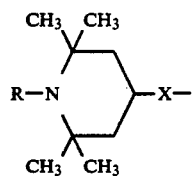 (V)

the group $-OR_1$; $-NRR_1$, wherein X, R and $R_1$ are as defined above; and
said compositions being in the form of a preparation suitable for topical application and consisting of lotions, ointments, creams, emulsions, gels and oils.

2. Cosmetic and dermatological compositions according to claim 1 wherein the compound of claim 1 is contained in the preparation in a free-radical deactivating effective amount.

3. Cosmetic and dermatological compositions according to claim 1 containing from 0.05 to 10% by weight of a compound of formula I.

4. Cosmetic and dermatological compositions according to claim 1 containing from 0.1 to 5% by weight of a compound of formula I.

* * * * *